(12) United States Patent
Jansen et al.

(10) Patent No.: US 8,082,918 B2
(45) Date of Patent: Dec. 27, 2011

(54) INHALER

(75) Inventors: Rob Jansen, Loughborough (GB); Lars Knudsen, Struer (DK); Henrik Vilstrup, Struer (DK)

(73) Assignee: AstraZeneca AB, Sodertalje (SE)

( * ) Notice: Subject to any disclaimer, the term of this patent is extended or adjusted under 35 U.S.C. 154(b) by 1007 days.

(21) Appl. No.: 10/221,379

(22) PCT Filed: Mar. 16, 2001

(86) PCT No.: PCT/SE01/00561
§ 371 (c)(1),
(2), (4) Date: Nov. 13, 2002

(87) PCT Pub. No.: WO01/70317
PCT Pub. Date: Sep. 27, 2001

(65) Prior Publication Data
US 2003/0136401 A1 Jul. 24, 2003

(30) Foreign Application Priority Data
Mar. 18, 2000 (GB) .................................. 0006529.2

(51) Int. Cl.
*A61M 11/00* (2006.01)
(52) U.S. Cl. .......... 128/200.23; 128/200.14; 128/203.23
(58) Field of Classification Search ............. 128/200.14, 128/200.23, 203.12, 203.16, 204.26, 204.21, 128/204.23, 205.24, 203.23, 205.14, 205.19
See application file for complete search history.

(56) References Cited

U.S. PATENT DOCUMENTS

| | | | |
|---|---|---|---|
| 5,027,808 A | | 7/1991 | Rich et al. |
| 5,060,643 A | * | 10/1991 | Rich et al. ................. 128/200.23 |
| 5,119,806 A | * | 6/1992 | Palson et al. ............. 128/200.14 |
| 5,447,150 A | * | 9/1995 | Bacon ....................... 128/200.14 |
| 5,533,498 A | | 7/1996 | Sioutas |
| 5,826,571 A | * | 10/1998 | Casper et al. ............. 128/200.23 |
| 6,415,784 B1 | * | 7/2002 | Christrup et al. ........ 128/200.23 |

FOREIGN PATENT DOCUMENTS

| | | |
|---|---|---|
| EP | 0 045 419 | 2/1982 |
| GB | 1 269 811 | 4/1972 |
| GB | 1 297 993 | 11/1972 |
| GB | 2263068 | 7/1993 |
| GB | 2 263 873 A | 8/1993 |
| GB | 2 264 238 A | 8/1993 |
| GB | 2 279 571 A | 1/1995 |
| GB | 2 292 891 A | 3/1996 |
| JP | 10510742 | 10/1998 |

(Continued)

*Primary Examiner* — Darwin Erezo
(74) *Attorney, Agent, or Firm* — Finnegan, Henderson, Farabow, Garrett & Dunner, LLP

(57) ABSTRACT

A breath-actuated inhaler for delivery of a medicament by inhalation from a canister (2) which is compressible to deliver a dose of medicament. The inhaler comprises a housing (1) for holding a canister (2) and including a mouthpiece (5) for delivery of a dose of medicament from a canister (2) held in the housing; and an actuation mechanism (6) for compressing a canister (2) held in the housing (1) in response to inhalation at the mouthpiece (5). The housing includes two separable portions (19, 20). The first housing portion (19) mounts the actuation mechanism (6). The second housing portion (20) houses the mouthpiece (5) and a duct (24) shaped to direct an inhalation flow from the mouthpeice (5) to the first housing portion (19) for triggering the actuation mechanism (6). The duct (24) and the mouthpiece (5) are integrally formed and separable from the second housing portion (20).

11 Claims, 12 Drawing Sheets

FOREIGN PATENT DOCUMENTS

| | | |
|---|---|---|
| WO | 9200770 | 1/1992 |
| WO | WO 93/00241 | 12/1993 |
| WO | 9619253 | 6/1996 |
| WO | 9916490 | 4/1999 |
| WO | 9925407 | 5/1999 |
| WO | WO 99/49916 | 10/1999 |
| WO | WO 00/16835 | 3/2000 |
| WO | WO 00/16838 | 3/2000 |

* cited by examiner

INHALER

CROSS REFERENCE TO RELATED APPLICATIONS

The present application is a national phase application under 35 U.S.C. Section 371 filed from International Patent Application PCT/SE01/00561 filed 16 Mar. 2001, which claims priority to United Kingdom patent application Serial. No. 0006529.2, filed 18 Mar. 2000. The contents of these applications are incorporated herein by reference in their entirety.

The present application relates to a breath-actuated inhaler for delivery of medicament from a canister.

Inhalers are commonly used to deliver a wide range of medicaments. The inhaler holds a canister of medicament which is actuatable, for example by compression, to deliver a dose of medicament. A very simple, known type of inhaler consists of a plastic shell including a mouthpiece and a nozzle block for holding the valve stem of the canister and directing medicament delivered from the canister out of the mouthpiece. The body of the canister is exposed to allow the user to actuate the canister by compressing the canister body against the shell of the inhaler. This type of inhaler is commonly known as a press-and-breathe inhaler.

The present invention relates to a inhaler provided with an actuation mechanism for actuating the canister. In particular, the mechanism is breath-actuated, ie. arranged to actuate the canister in response to inhalation at the mouthpiece. Typically a breath-actuated inhaler includes a loading mechanism for loading a resilient loading element with an actuation force for compression of the canister. A triggering mechanism may be provided to hold the resilient loading element against compression of the canister, the triggering mechanism releasing the resilient loading element upon inhalation.

Inhalers with an actuation mechanism may be designed to be reusable. An expired canister may be removed and replaced by a fresh canister. Consequently such a reusable inhaler will have a longer lifetime and higher usage than a simple press-and-breathe inhaler which is cheap and typically supplied new with each canister.

According to the present invention, there is provided a breath-actuated inhaler for delivery of a medicament by inhalation from a canister which is compressible to deliver a dose of medicament, the inhaler comprising:

a housing for holding a canister and including a mouthpiece for delivery of a dose of medicament from a canister held in the housing; and an actuation mechanism for compressing a canister held in the housing in response to inhalation at the mouthpiece, wherein the housing includes two separable portions, the first portion mounting the actuation mechanism and the second portion housing the mouthpiece and a duct shaped to direct an inhalation flow from the mouthpiece to the second portion for triggering the actuation mechanism.

The high usage of an inhaler having an actuation mechanism can cause a number of different problems. For example the duct may become dirty which is undesirable because of the risk of contamination when the user inhales. Similarly, the duct can become clogged up which is undesirable because it may restrict the inhalation flow required to actuate the inhaler and risk the mechanism failing to operate upon inhalation. Another problem which can occur is that the mouthpiece becomes progressively damaged by the user's teeth when the mouthpiece is inserted in the mouth. However, the present invention allows the mouthpiece and/or duct to be replaced and/or removed for cleaning because the second portion holding these elements is separable from the first portion which mounts the actuation mechanism.

Preferably, the duct is separable from the second portion of the housing. This is particularly advantageous because it allows the duct to be replaced whilst retaining the second portion of the housing. This is advantageous because it minimises the number of parts which need to be replaced. Also, separation of the duct from the second portion of the housing facilitates cleaning of the duct.

Advantageously, the duct and the mouthpiece are an integrally formed. This allows the duct and mouthpiece to be replaced together. For example, the integral duct and mouthpiece may be supplied with each new canister.

The present invention is advantageously applied to an inhaler wherein the first portion of the housing has a flow inlet for receiving said inhalation flow and the duct is shaped to direct the inhalation flow to the flow inlet.

Desirably, the actuation mechanism includes a vane responsive to said inhalation flow for triggering the actuation mechanism and the first portion of the housing houses a further duct shaped to direct inhalation flow from the flow inlet to the vane. Thus the duct housed in the second portion of the housing and the further duct together define a composite duct from the mouthpiece to the vane. This allows the inhalation flow to be controlled by the shape of the duct which is important to allow proper operation of the actuation mechanism.

To allow better understanding, an inhaler which embodies the present invention will now be described by way of non-limitative example with reference to the accompanying drawings, in which.

Figure 1:
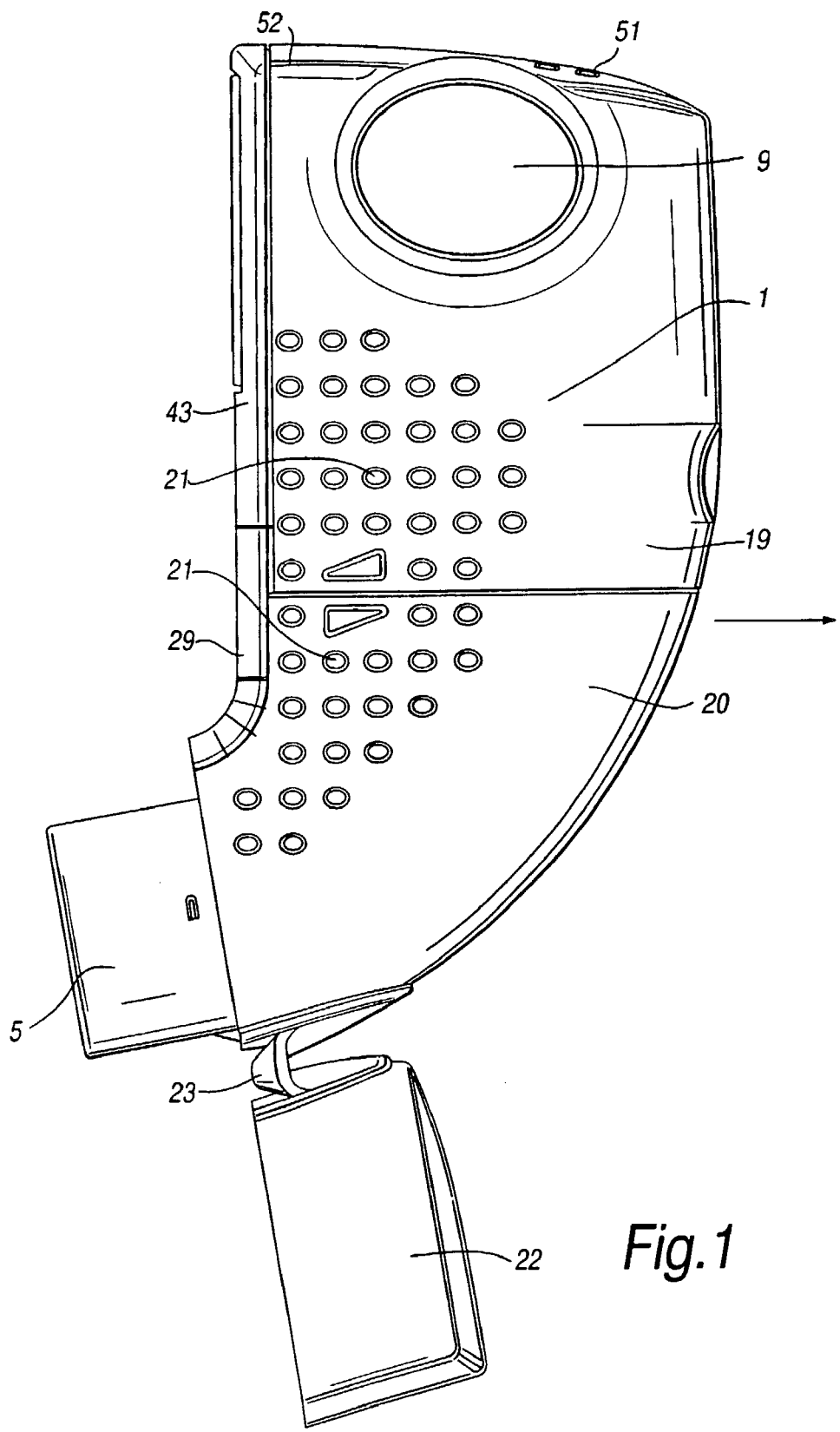
FIG. 1 is a side view of the inhaler.

As illustrated in FIG. 1, the inhaler has a housing 1 comprising an upper portion 19 and a lower portion 20. As illustrated in the cross-sectional view of FIG. 2, the upper housing portion 19 is a hollow shell which holds a canister 2 of medicament having a generally cylindrical body 3 held with its axis in a predetermined direction, vertical in FIG. 2. The upper housing portion 19 houses an actuation mechanism for actuating the canister 2 which will be described in more detail below.

The interior of the upper housing portion 19 is open to the atmosphere by means of air inlets 51 formed in the upper wall 52 of the upper housing portion 19. The location of the air inlets 51 minimises occlusion by the users hand which will normally grip the sides of the housing 1 and not cover the upper wall 52.

The canister 2 is compressible to deliver a dose of medicament. In particular the canister 2 has a valve stem 4 which is compressible relative to the body 3 to deliver a dose of medicament from the valve stem 4. The canister is of a known type including a metering chamber which captures a defined volume the medicament from the body 3 of the canister 2. This volume of medicament is delivered as a metered dose from the valve stem 4 on compression of the valve stem 4 relative to the body 3. The valve stem 4 is weakly biased outwardly by an internal valve spring (not shown) to reset the canister 2 after compression for refilling the metering chamber.

The lower housing portion 20 is a hollow shell connected to the upper housing portion 19 by a sliding joint (not shown) which allows the lower portion 20 to be separated in the direction of the arrow in FIG. 1 by the user gripping textured surfaces 21 formed on the upper and lower housing portions 19 and 20. A cap 22 is hinged to the lower housing portion 20 by a flexible joint 23 to cover and uncover a mouthpiece 5 protruding from the lower housing portion 20.

Figure 2:
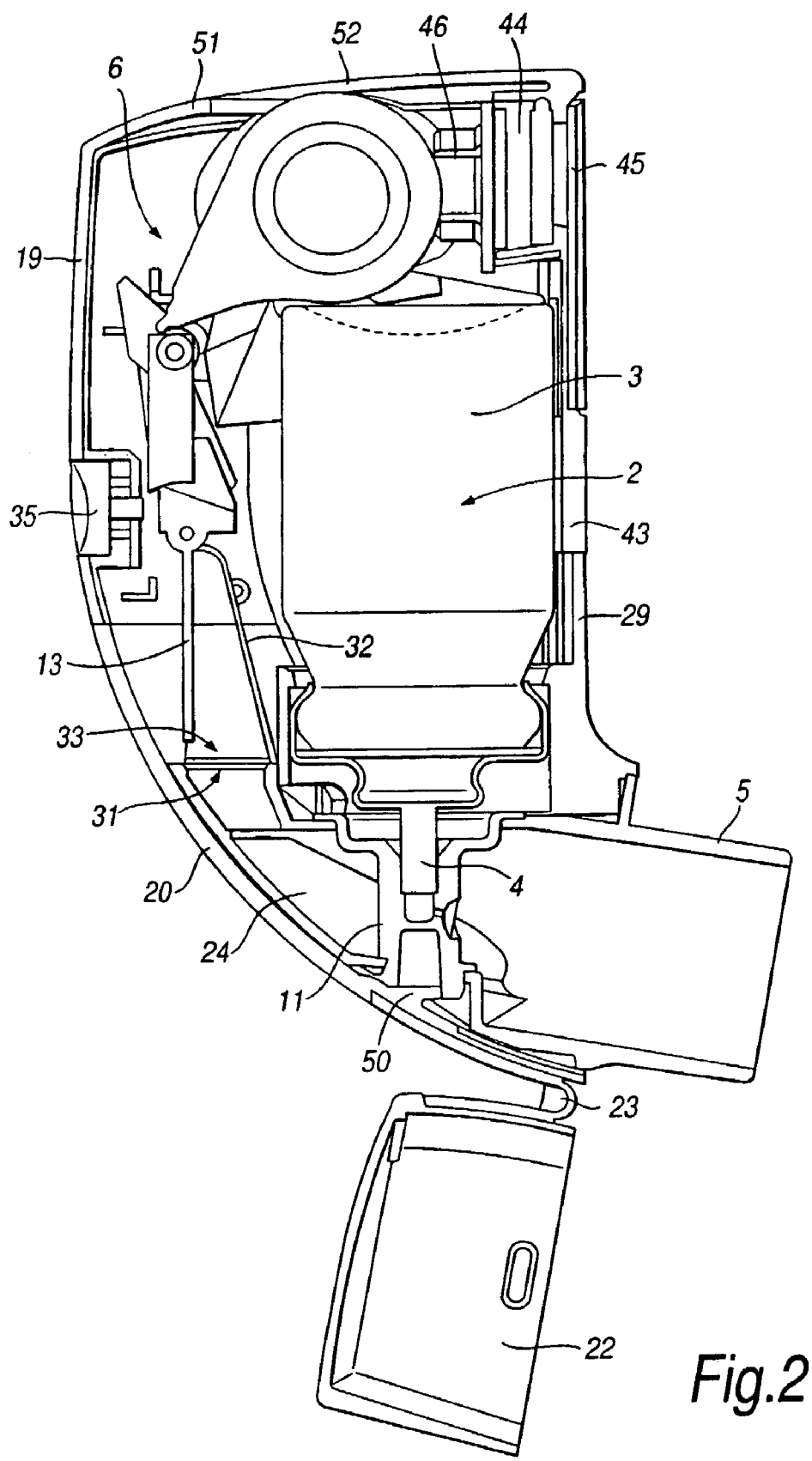
FIG. 2 is a cross-sectional view of the inhaler illustrating the housing and duct.
Figure 3:
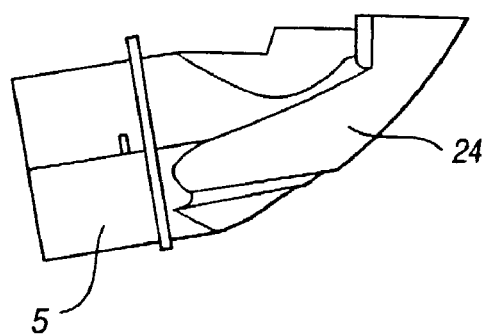
FIG. 3 is a side view of the duct.

As shown in FIG. 2, the lower housing portion 20 houses a duct 24 which is integrally formed with the mouthpiece 5, as illustrated in isolation in FIG. 3.

Figure 4:
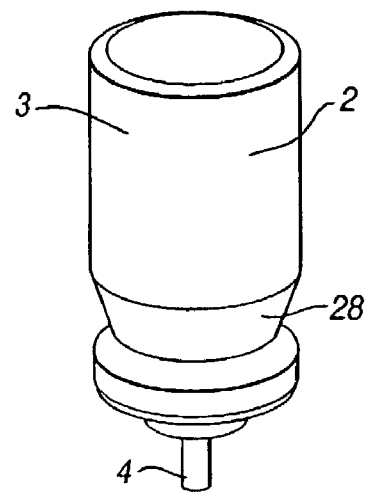
FIG. 4 is a side view of the canister and duct assembled together.
Figure 4:
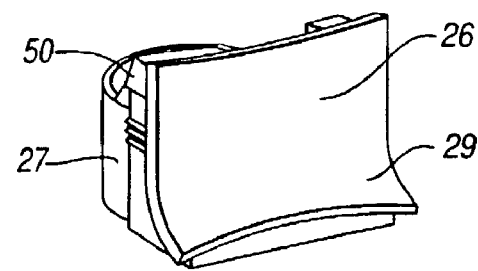
Figure 4:
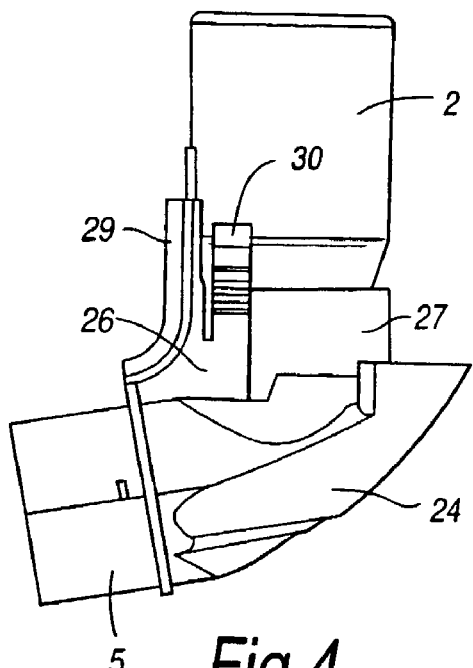
Figure 5:
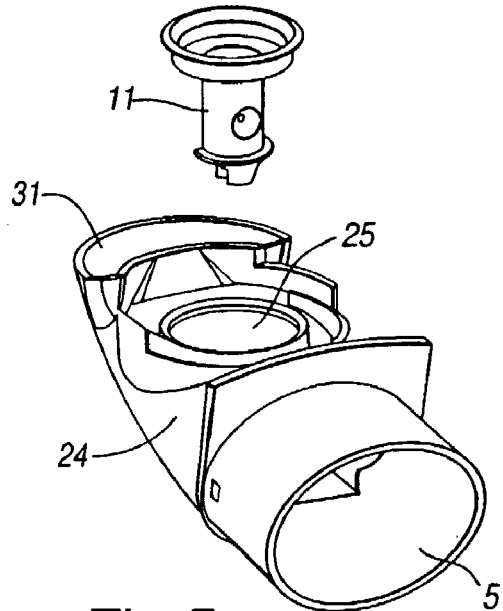
FIG. 5 is an exploded view of the canister, collar and duct.
Figure 6:
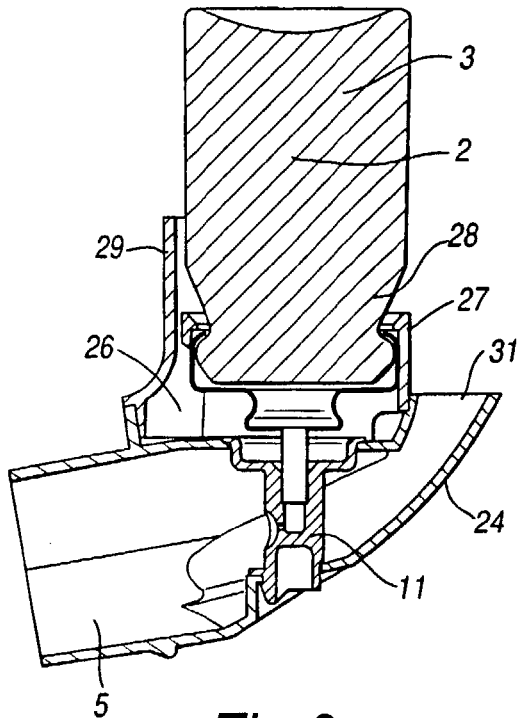
FIG. 6 is a cross-sectional view of the canister and dust assembled together.

The duct 24 is assembled with a canister 2 as shown in FIGS. 4 to 6. The duct 24 receives a nozzle block 11 in an opening 25. The valve stem 4 of the canister is received in the nozzle block 11 which is arranged to direct a dose of medicament delivered from the valve stem 4 out of the inhaler through the mouthpiece 5. The duct 24 and nozzle block 11 are separately formed. This allows each to be manufactured and subsequently assembled. This produces manufacturing and logistical savings because it facilitates different nozzle block designs being incorporated with a single duct design and vice versa.

A collar 26 is permanently connected to the canister 2. The collar 26 includes an annular retaining ring 27 permanently fitted around a necked portion 28 of the canister body 3. The retaining portion 27 prevents removal of the collar 26 from the canister such that the collar 26 is removed and replaced together with the canister 2. However, the retaining portion 27 and the canister 2 have a small degree of relative movement along the axis of the canister 5 to allow compression of the canister body 2 towards the valve stem 4.

The collar 26 further includes a front panel 29 integrally formed with the retaining ring 27. When the canister 2 is inserted in the housing 1, the front panel 29 of the collar 26 closes an opening formed between the upper housing portion 19 and the lower portion 20 and therefore forms a part of the outer wall of the housing 1. Accordingly, the presence or absence of the front panel 29 provides a visual indication to the user of whether or not a canister 2 has been inserted in the canister, because the collar 26 is permanently connected to the canister 2.

A pair of catch arms 30 integrally formed with the front panel 29 of the sides of the collar 26 catch the interior surface of the upper housing portion 19 to hold the collar 26 and the canister 2 in the upper housing portion 19.

The lower housing portion 20 has a stud 50 which locates the end of the nozzle block 11 as shown in FIG. 2 to hold the lower housing portion 20 and the duct 24 in place relative to one another. However, the lower housing portion 20 is not retained on the duct 24, so may be removed from the upper housing portion 19 leaving the canister 2 inserted in the upper housing portion 19 and the duct 24 held on the canister 2 by the valve stem 4 being inserted in the nozzle block 11. The duct 24 and nozzle block 11 may subsequently be slid off the valve stem 4 for cleaning or replacement. The canister 2 and collar 26 may be slid out from the upper housing portion 19 after depression of the catch arms 30. Subsequently a replacement canister 2 and collar 26 may be inserted.

Typically a new duct 24 and nozzle block 11 will be provided to the user with each new canister 2 so that the duct 24 and mouthpiece 5 are regularly replaced to prevent damage or dirt building up over time. The duct 24 has an opening 31 at its end opposite from the mouthpiece 5.

As shown in FIG. 2, the upper housing portion 19 holds a flap duct 32 which extends from a flow inlet 33 to a flap 13 which forms part of the triggering mechanism for the actuation mechanism as described in detail below. Therefore the duct 24 housed in the lower housing portion 19 and the flap duct 32 together define a composite duct shaped to direct the inhalation flow from the mouthpiece 5 to the flap 13. The composite duct formed by the duct 24 and the flap duct 32 is shaped to control the flow to the flap 13 to provide appropriate flow characteristics for proper operation of the flap 13.

The inhaler is further provided with an actuation mechanism 6. To assist understanding, a general description of the overall structure and operation of the actuation mechanism 6 will first be given.

An actuation force for compressing the canister 2 is stored in a resilient loading element in the form of a torsion spring 7. To load the torsion spring 7, the actuation mechanism 6 includes a loading mechanism consisting of a loading member in the form of a rotatable spindle 8 and two contact members in the form of buttons 9 which protrude from the housing as shown in FIG. 1. Depression of the buttons 9 towards one another, relative to the housing 1, drives the loading member 8 to load the torsion spring 7 through a cam arrangement between the buttons 9 and spindle 8.

The torsion spring 7 biases compression of the canister 2 by engaging a canister engagement member in the form of a lever 10 which depresses the body 3 of the canister towards the stem 4 held in the nozzle block 11.

To allow storage of the actuation force in the torsion spring 7 after loading, the actuation mechanism 6 includes a triggering mechanism. This includes a locking lever 12 which holds the canister engagement lever 10 against compression of the canister 2. To release the canister engagement lever 10, the triggering mechanism further includes a vane in the form of a flap 13 which in a rest state holds the locking lever 12 in place. Inhalation at the mouthpiece 5 moves the flap 13 to release the locking member 12. This in turn releases the canister engagement lever 10 allowing the torsion spring 7 to drive compression of the canister 2.

The actuation mechanism 6 further includes a locking mechanism which locks the spindle 8 after loading of the torsion spring 7, thereby holding the torsion spring 7 in its loaded state before triggering and locking the canister in its compressed state after triggering.

The locking mechanism includes a catch 14 which, in a locking position, catches the spindle 8 and holds the torsion spring 7 in its loaded state. The locking mechanism further includes an intermediate member 15. A resilient biasing element in the form of a spring 16 is provided between the catch 14 and the intermediate member 15 to bias the catch 14 towards its locking position. The spring 16 allows deflection of the catch 14 by the spindle 8 during loading of the torsion spring 7.

Prior to inhalation the intermediate member 15 is held in place by the canister engagement lever 10. Upon inhalation at the mouthpiece 5, the flap 13 engages the intermediate member 15 to hold it in place. After compression by the canister engagement lever 10, the canister 2 is locked in its compressed state by the catch 14 of the locking mechanism holding the spindle 8 in place.

When the level of inhalation at the mouthpiece falls below a predetermined threshold, the flap 13 releases the intermediate member 15 to unload the biassing element 16 which in turn allows the catch 14 to release the spindle 8. After release by the catch 14, the spindle 8, torsion spring 7 and canister engagement lever 10 move upwardly and the canister resets.

Figure 7:
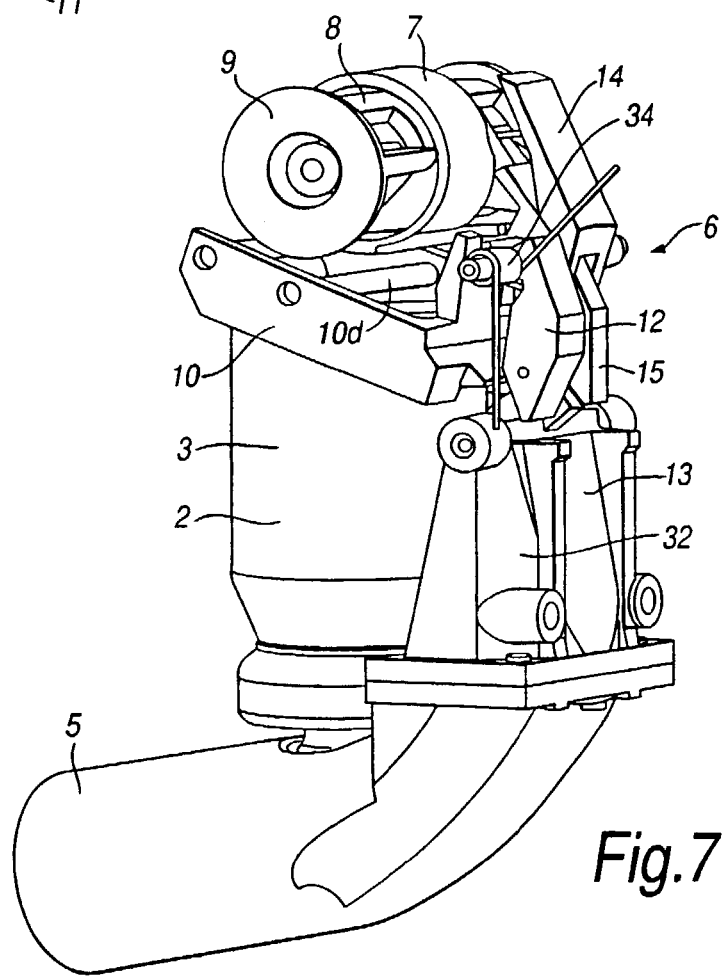
FIG. 7 is a view from the side and rear of the actuation mechanism.

Now there will be given a detailed description of the actuation mechanism 6, the entirety of which is illustrated in FIG. 7 and parts of which are illustrated in FIGS. 8 to 13.

Figure 8:
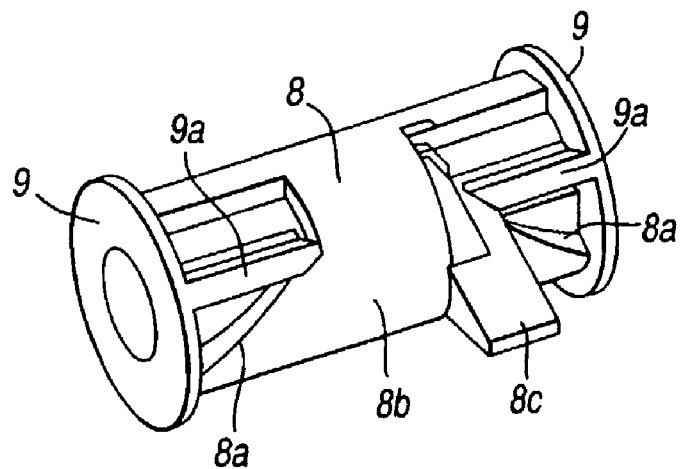
FIG. 8 is a view from the rear of the spindle.

The loading mechanism is illustrated in FIG. 8 and consists of a rotatable spindle 8 and two contact members in the forms of buttons 9 at both ends. The spindle 8 is rotatably mounted in the upper housing portion 19 about an axis orthogonal to the axis of the cylindrical body 3 of the canister 2. The spindle 8 has a pair of cam surfaces 8a disposed on opposite sides of the rotational axis of the spindle 8. The buttons 9 are mounted in the housing to be movable in a movement direction parallel to the rotational axis of the spindle 8. The buttons 9 each have a pair of inwardly projecting cam followers 9a which each engage a respective cam surface 8a of the spindle 8. The cam arrangement of the cam surfaces 8a and the cam followers 9a between the spindle 8 and the buttons 9 causes depression of the buttons 9 to drive rotation of the spindle 8.

Figure 9:
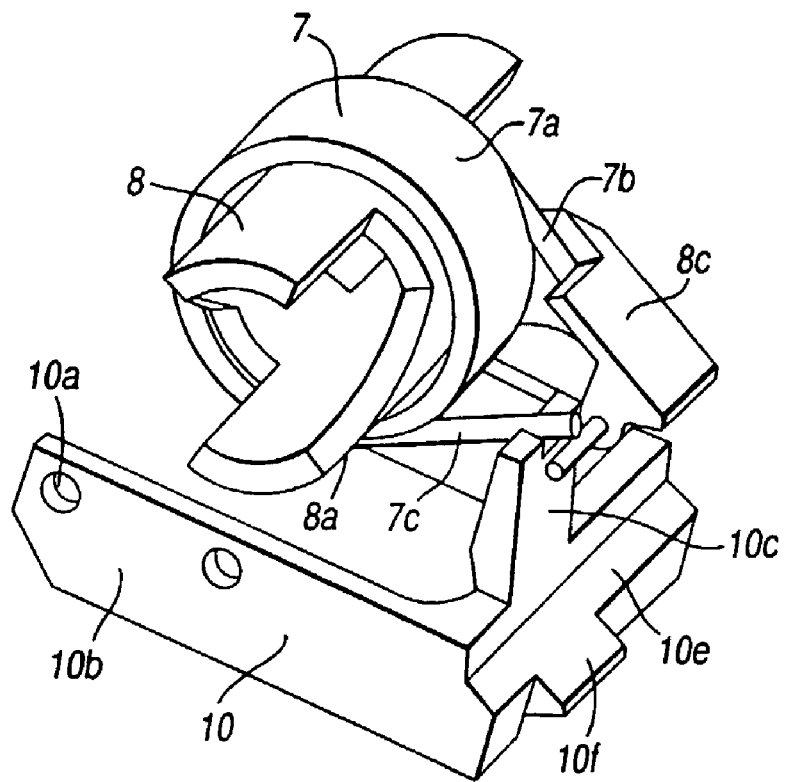
FIG. 9 is a view from the side, rear and above showing the arrangement of the resilient loading element.

As illustrated in FIG. 9, the torsion spring 7 which forms the resilient loading element is disposed with its coils 7a encircling a central cylindrical surface 8b of the spindle 8. A catch arm 8c protrudes radially from the spindle 8. A first leg 7b of the torsion spring 7 is restrained by the catch arm 8c so that the movement of the spindle 8 driven by the buttons 9 loads the torsion spring 7.

Figure 10:
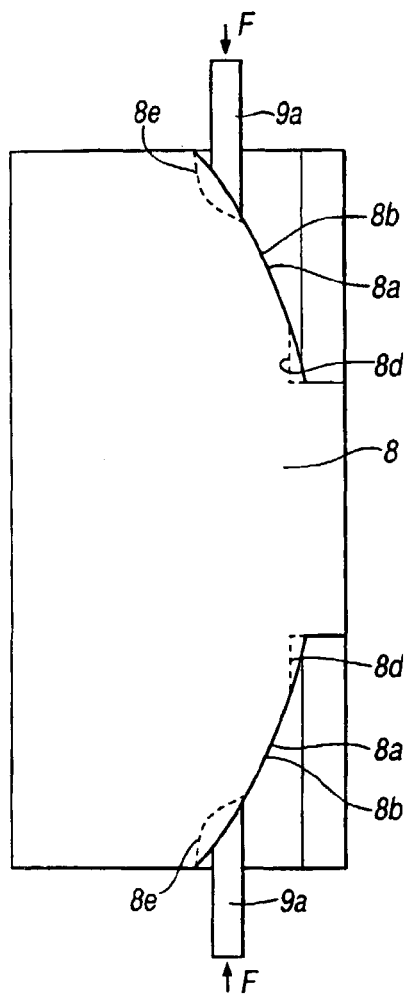
FIG. 10 is a schematic view of the cam surfaces formed on the spindle.

As illustrated schematically in FIG. 10, the cam surfaces 8a have a non-linear shape which causes the gearing ratio of the amount of driven movement of the spindle 8 to the amount of movement of the buttons 9 to be a non-linear function of the rotational position of the spindle 8. The major portion 8b of each cam surface 8a is shaped with increasing pitch to compensate for the increased reactive loading force applied by the torsion spring 7 to the spindle 8 as the buttons 9 are depressed. In particular, they are shaped such that the necessary force applied to the buttons is substantially constant so the user feels a linear resistance. As the torsion spring 7 has a linear spring constant, this is achieved by shaping the major portion 8b of each cam surface 8a such that the gearing ratio is inversely proportion to the rotational position of the spindle 8.

Optionally, the outermost portion of the cam surfaces 8a which are contacted by the cam followers 9a during the initial portion of the driven movement of the spindle may have a decreased pitch, for example as illustrated by the dotted lines 8e. This is to reduce the gearing ratio relative to the subsequent major portion 8b. In this way the user initially feels a low resistance to movement of the buttons 9. This improves the feel perceived by the user and also assists the user in applying force.

Another option is to provide the final portion of the cam surface 8a with a detent, for example as illustrated by the dotted lines 8d. When the end of the cam followers 9a reach the detent 8d, the cam surface 8a of the spindle 8 no longer exerts a force urging the buttons outwardly on the buttons 9. At this position the detent 8d is urged by the torsion spring 7 against the side of the cam followers 9a and therefore holds the buttons 9 in their innermost position. This prevents the buttons 9 from loosely sliding back and forth after the torsion spring 7 has been loaded.

As shown in FIG. 9, the torsion spring 7 engages a canister engagement lever 10 which is pivotally mounted to the interior of the housing about an axis 10a. The canister engagement lever 10 is generally U-shaped with two parallel sides 10b connected by a cross piece 10c. A bar 10d extending between the two sides 10b bears on the body 5 of the canister 2. A mount 10e formed on the cross-piece 10c is engaged by the second leg 7c of the torsion spring 7, whereby loading of the torsion spring 7 biasses the lever 10 to compress the canister 2. The canister engagement lever 10 is biassed upwardly by a reset spring (not shown), which may be arranged as a torsion spring on the axis 10a, but this is weaker than the torsion spring 7.

The torsion spring 7, spindle 8 and canister engagement lever 10 are all rotatable about axis orthogonal to the cylindrical axis of the body 5 of the canister 2. This provides a simple and reliable loading mechanism particularly because of the arrangement of the torsion spring 7 with its coils 7a encircling the spindle 8. Some or all of these elements could alternatively be linearly movable in a plane parallel to the cylindrical axis of the body 5 of the canister 2 to achieve a loading mechanism which is equally simple to construct. However rotatable elements are preferred from the point of view of reliability in repeated use of the actuation mechanism 6.

On the other hand, the movement of the buttons in a direction orthogonal to the cylinder axis of the body 3 of the canister 2 assists the user in application of force to the loading mechanism. As typical for inhalers, the housing 1 extends in the direction of the cylindrical axis of the body 3 of the canister 2, so may be easily held in the palm of a hand with the buttons 9 protruding from either side. Thus the buttons 9 are easily depressed between a finger and thumb. Alternatively a single button could be provided allowing loading in a similar manner by the user pressing the button and the housing on the opposite side to the button. Either configuration also allows loading by laying the inhaler on a surface and applying force for example with the palm of a hand. This facilitates loading by a user with limited finger control or movement, for example a chronic arthritis sufferer.

Figure 11:
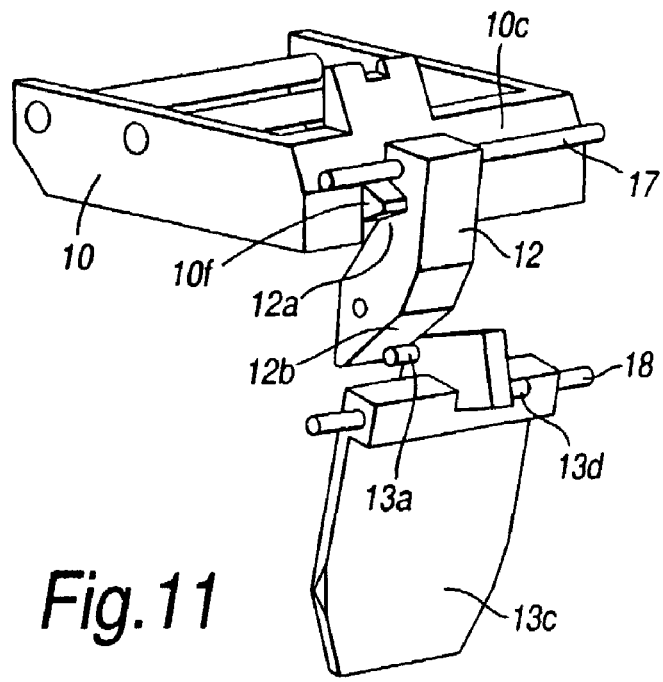
FIG. 11 is a view from the side and rear of the triggering mechanism.
Figure 12:
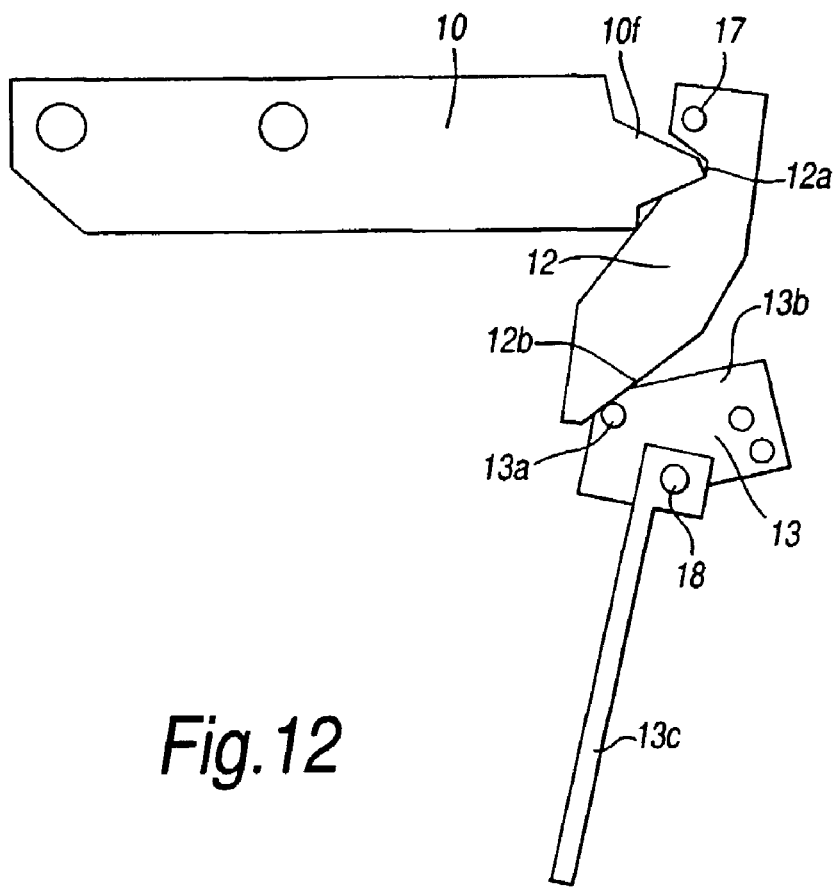
FIG. 12 is a side view of the triggering mechanism.

The actuation member mechanism 6 includes a triggering mechanism as illustrated in FIGS. 11 and 12 which allows storage of the actuation force in the torsion spring 7 after loading.

The triggering mechanism includes a locking lever 12 which is pivotably mounted on an axle 17 extending across the interior of the housing 1. The locking lever 12 has a notch 12a adjacent the axle 17. In a reset state shown in FIG. 12, the notch 12a holds a protrusion 10f protruding from the cross-piece 10c of the canister engagement lever 10, thereby holding the lever 10 against compression of the canister 2. The locking lever 12 is weakly biassed towards the position shown in FIGS. 11 and 12 by a reset spring 34 arranged as a torsion spring on the axle 17.

The triggering mechanism further includes a vane in the form of a flap 13 which is rotatably mounted on an axle 18 extending across the interior of the housing 1. The flap 13 biassed by a reset spring (not shown), which may be arranged as a torsion spring on the axle 18, towards the position shown in FIG. 12. The flap 13 has a locking lever engagement surface 13a which protrudes from a block 13b positioned above the axle 18. In the position shown in FIG. 12, the engagement surface 13a engages a contact surface 12b formed on the end of the locking lever 12 distal from the axle 17 to hold the locking lever 12 in place holding the canister engagement lever 10.

The flap 13 is disposed in the composite duct formed by the duct 24 and the flap duct 32 extending from the mouthpiece 5 with a flap portion 13c extending across the composite duct at the opposite end from the mouthpiece 5, where the duct opens into the interior of the housing 1. Therefore, the flap 13 is responsive to inhalation at the mouthpiece 5.

Inhalation of the mouthpiece draws the flap portion 13c into the flap duct 32 (clockwise in FIG. 2 and anticlockwise in FIG. 12). Such rotation of the flap 13 allows the locking lever engagement surface 13a to move out of contact with the contact surface 12b of the locking lever 12.

The upper housing portion 19 also mounts a button 35 disposed adjacent the flap 13 above the axle 18 so that depression of the button 35 rotates the flap 13 in the same direction as inhalation at the mouthpiece 5. Therefore, the button 35 allows the actuation mechanism 6 to be manually released without inhalation at the mouthpiece 5, for example to allow actuation of the canister 2 for testing.

When the canister engagement lever 10 is loaded by the torsion spring 7, release of the locking lever 12 by the flap 13 allows the canister engagement lever 10 to be driven to compress the canister 2. The protrusion 10f deflects the locking lever 12 (anticlockwise in FIG. 12) as the canister engagement lever 10 passes.

Figure 13:
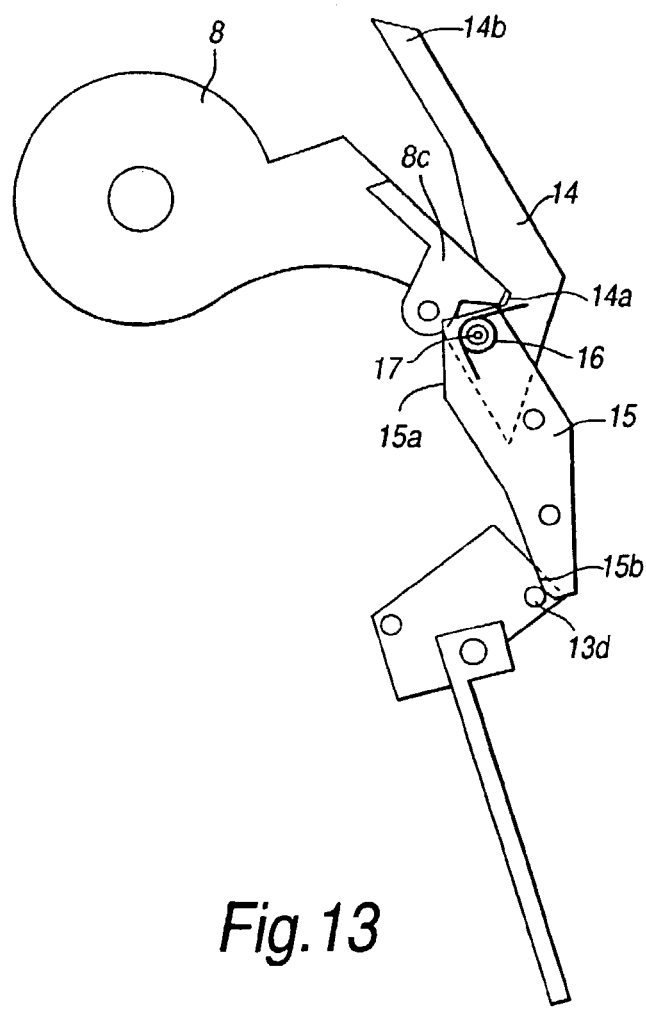
FIG. 13 is a side view of the locking mechanism.

As illustrated in FIG. 13, the actuation mechanism 6 further includes a locking mechanism for locking the spindle 8 after loading of the torsion spring 7. The locking mechanism comprises a catch 14 and an intermediate member 15 which are both pivotally mounted on the axle 17, adjacent the locking lever 12. Before compression of the canister 2, the intermediate member 15 is held in the position illustrated in FIG. 13 by the cross-piece 10c of the canister engagement lever 10 contacting a first contact surface 15a adjacent the axle 17. A resilient biassing element in the form of a torsion spring 16 is connected between the catch 14 and the intermediate member 15 and loaded to bias the catch 14 towards its locking position shown in FIG. 13.

The catch 14 has a notch 14a adjacent the axle 17 for engaging the arm 8c of the spindle 8 after rotation to the position illustrated in FIG. 13 where the torsion spring 7 is loaded. In this position, the loading provided by the spring 16 prevents release of the spindle 8 and thereby holds the torsion spring 7 in its loaded state. Before loading, the arm 8c of the spindle 8 is positioned above the end 14b of the catch 14 distal from the axle 17. When the spindle 8 is driven downwards by depression of the buttons 9, the arm 8c of the spindle engages the end 14b of the catch 14 and deflects the catch 14 by compressing the spring 16 to allow passage of the arm 8c of the spindle 8.

The flap 13 further includes a stud 13d protruding from the block 13b on the opposite side of the axle 18 from the locking lever engagement surface 13a. Upon inhalation at the mouthpiece 5, the flap 13 moves to the position illustrated in FIG. 13 where the stud 13d engages a second contact surface 15b of the intermediate member 15 distal from the axle 17. Prior to this point, the stud 13d does not contact the second contact surface 15b but the intermediate member 15 has been held in place by the canister engagement lever 10. Movement of the flap 13 triggers the triggering mechanism to release the canister engagement member 10 which moves downwards out of contact with the intermediate member 15. However, the stud 13d catches the contact surface 15b and so continues to hold the intermediate member 15 with the spring 16 loaded. Accordingly, the catch 14 remains in its locking position locking the spindle 8 by engagement of the arm 8c of the spindle 8 in the notch 14a of the catch 14.

Subsequently, when the level of inhalation of the mouthpiece falls below a predetermined threshold, the flap moves out of contact with the intermediate member 15 (clockwise in FIG. 13). The level of the predetermined threshold at which the flap 13 releases the intermediate member 15 is controlled by the shape of the second contact surface 15b of the intermediate member 15.

After release by the flap 13, the intermediate member 15 is driven by spring 16 which unloads (clockwise in FIG. 13). Such unloading of the spring 16 reduces the force by which the catch 14 is biassed towards its locking position. Accordingly, the force of the torsion spring 7 acting on the canister engagement lever 10 is sufficient to force the catch arm 8c of the spindle 8 out of the notch 14a. Accordingly, the spindle 8, the torsion spring 7 and canister engagement lever 10 are able to move upwardly biassed by the reset spring acting on the canister engagement lever 10, thereby allowing the canister to reset.

Figure 14A:
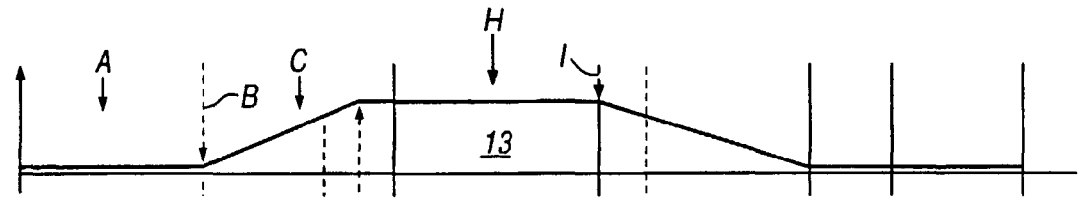
FIGS. 14A to 14F are graphs showing the angular positions of the elements of the actuation mechanism during its operation sequence.
Figure 14B:
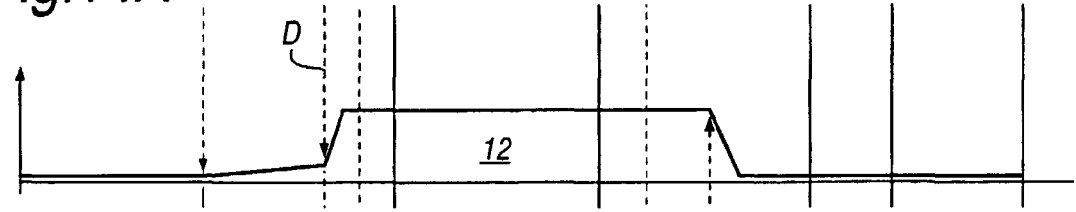
Figure 14C:
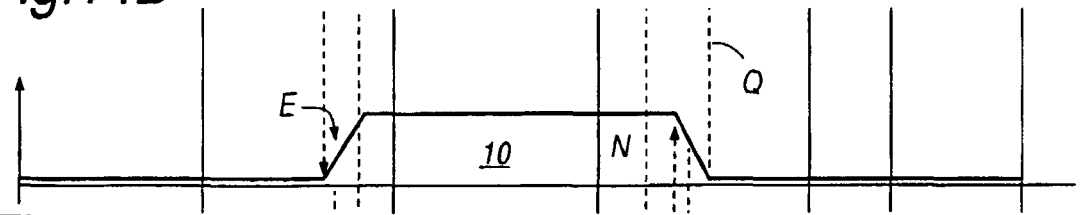
Figure 14D:
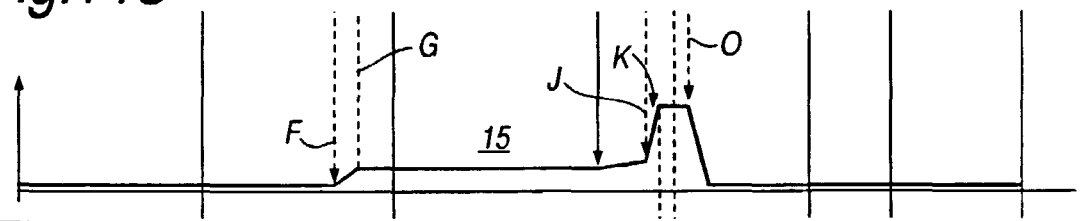
Figure 14E:
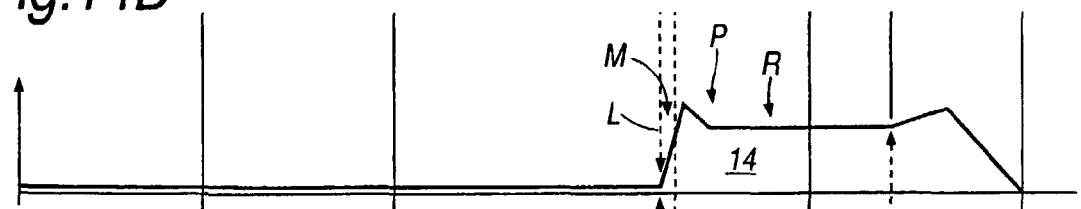
Figure 14F:
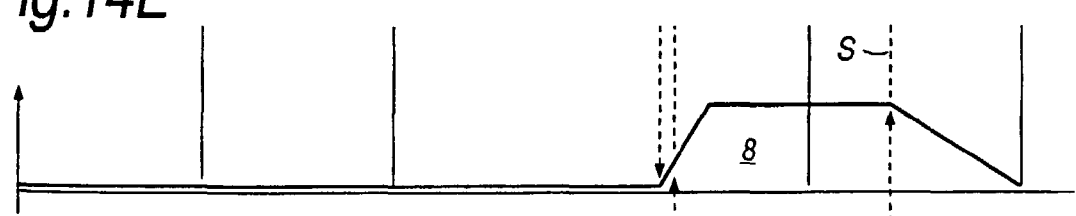

The sequence of operation of the actuation mechanism 6 will now be described with reference to FIGS. 14 to 22. FIGS. 14A to 14F are graphs showing the angular positions of the various elements of the actuation mechanism 6. In particular, FIG. 14A illustrates the angular position of the flap 13; FIG. 14B illustrates the angular position of the locking lever 12; FIG. 14C illustrates the angular position of the canister engagement lever 10; FIG. 14D illustrates the angular position of the intermediate member 15; FIG. 14E illustrates the angular position of the catch 14; and FIG. 14F illustrates the angular position of the spindle 8. Various states and positions of the actuation mechanism 6 are labelled by the letters A to R in FIG. 14 and FIGS. 15 to 22 illustrate the actuation mechanism 6 in some of these states with the views from opposite sides being suffixed by the letters A and B, respectively.

Figure 15A:
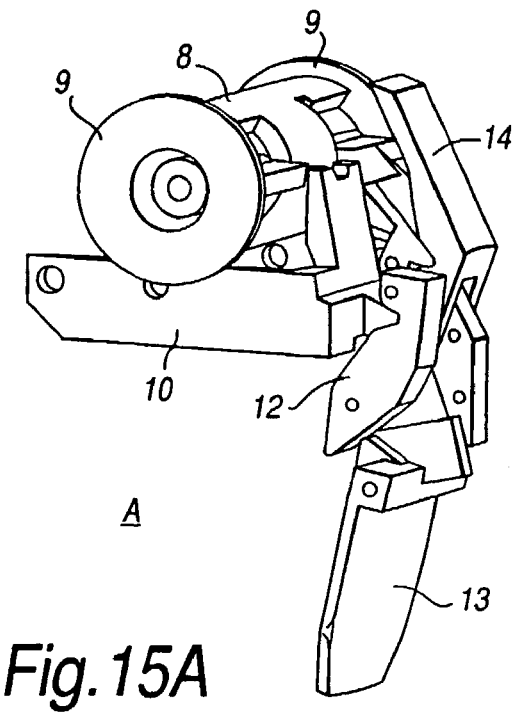
FIGS. 15 to 22 are views of the actuation mechanism in various states during its operation sequence with views from opposite sides being suffixed by the letters A, B respectively.
Figure 15B:
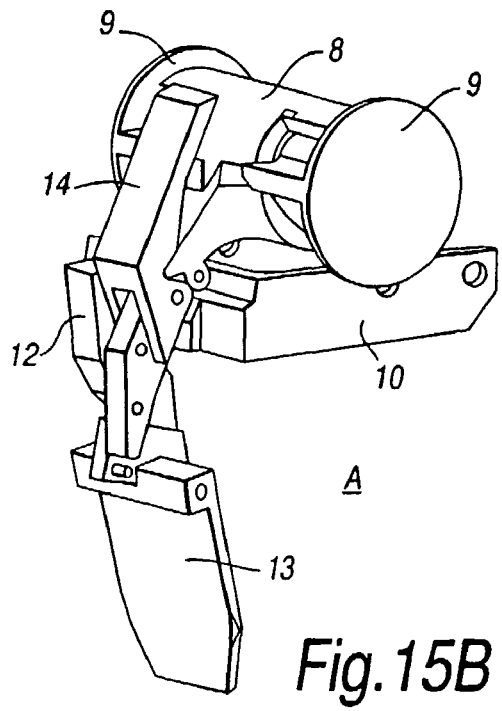
Figure 16A:
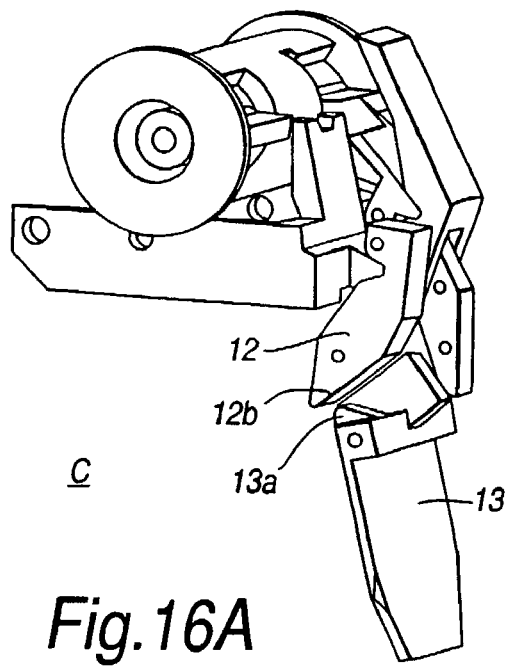
Figure 16B:
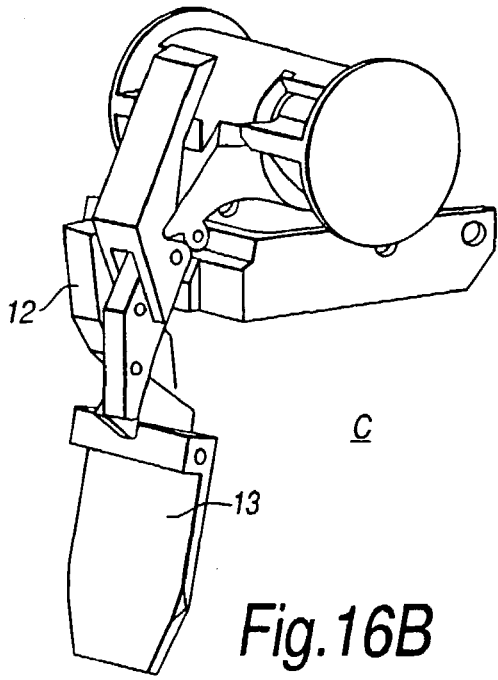
Figure 17A:
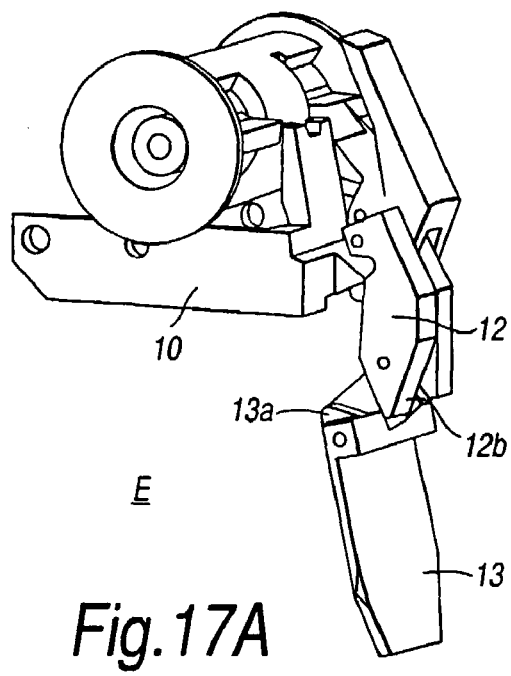
Figure 17B:
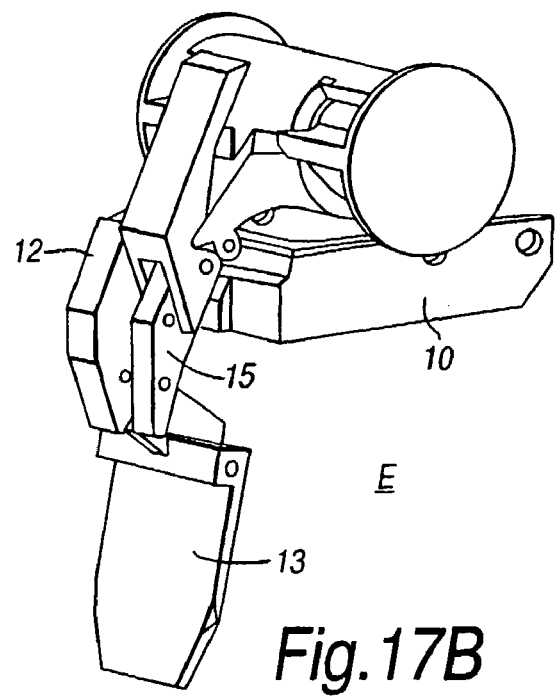
Figure 18A:
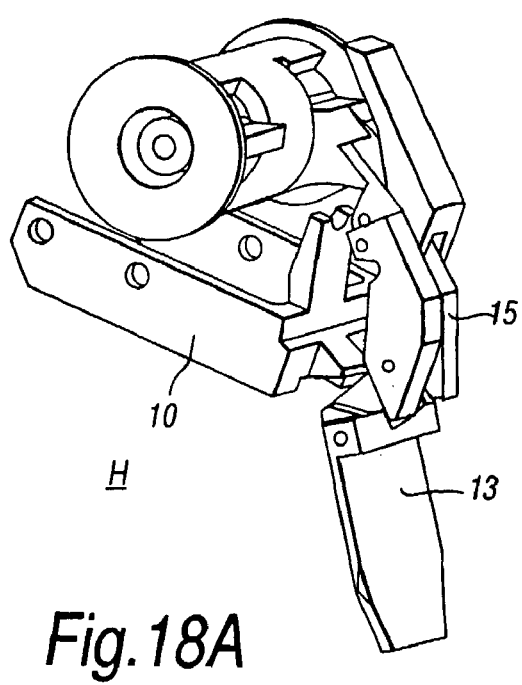
Figure 18B:
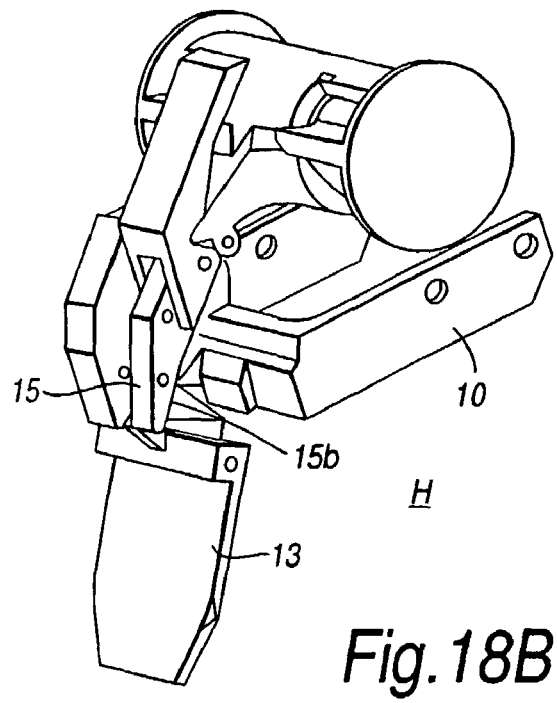
Figure 19A:
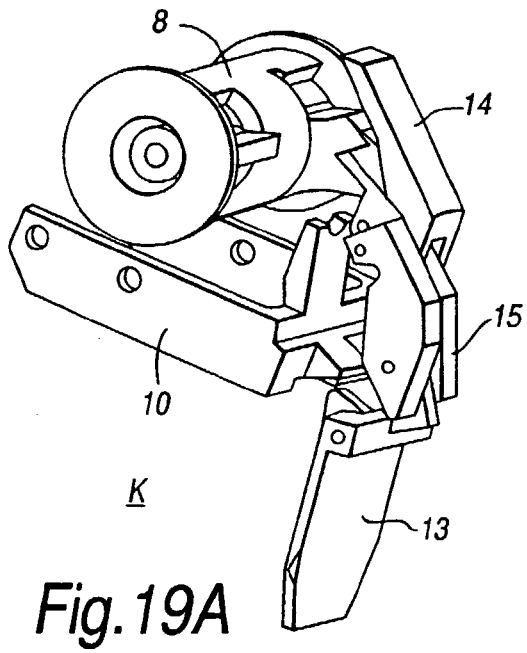
Figure 19B:
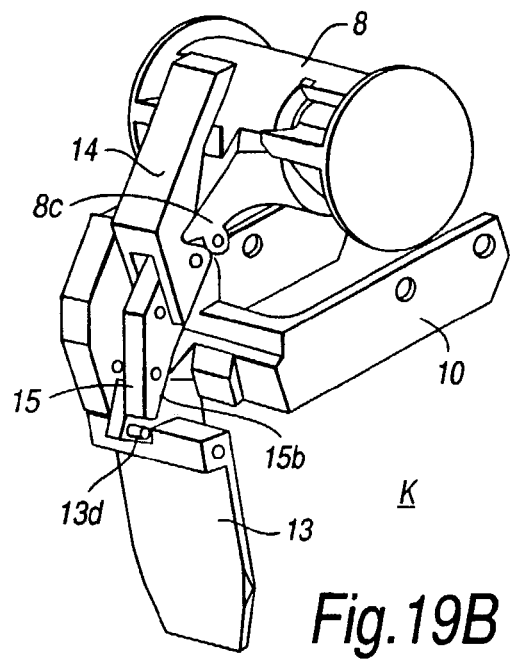
Figure 20A:
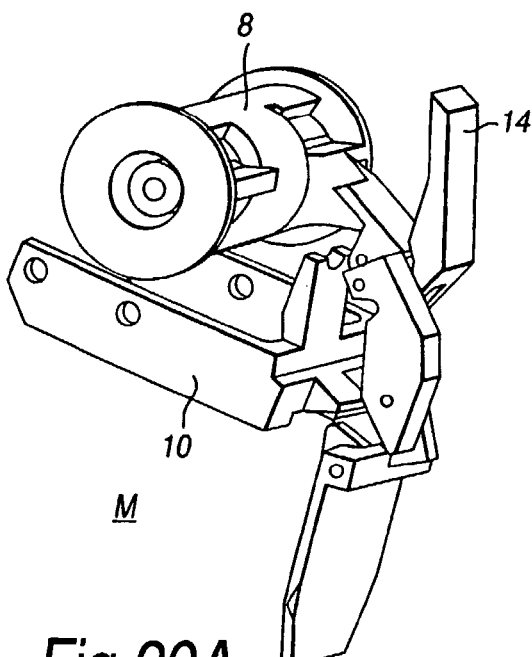
Figure 20B:
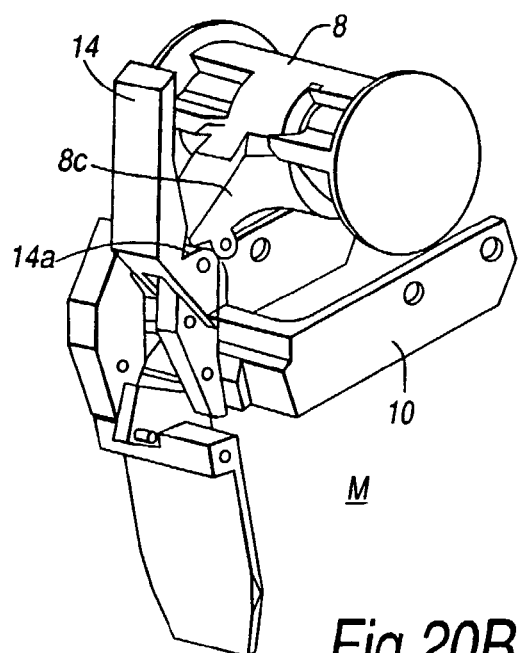
Figure 21A:
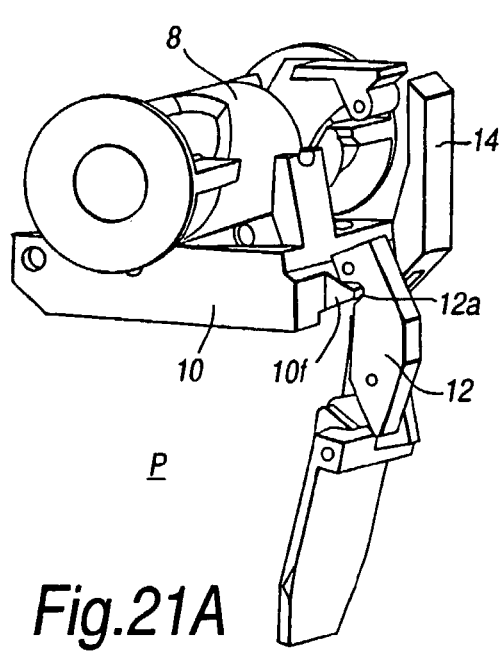
Figure 21B:
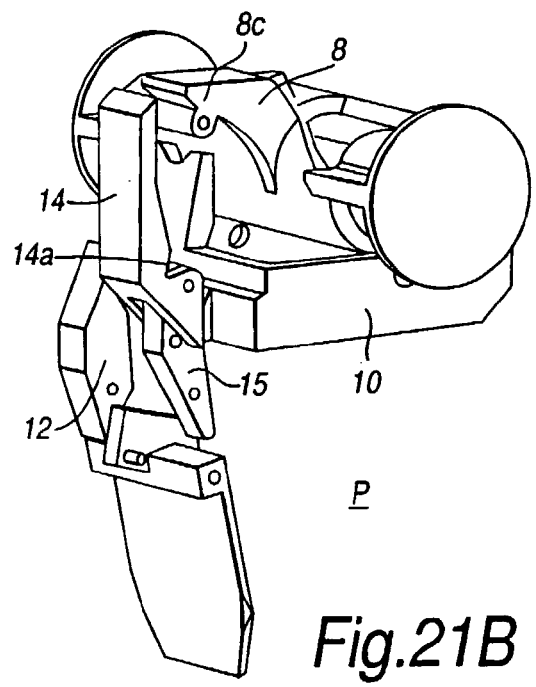
Figure 22A:
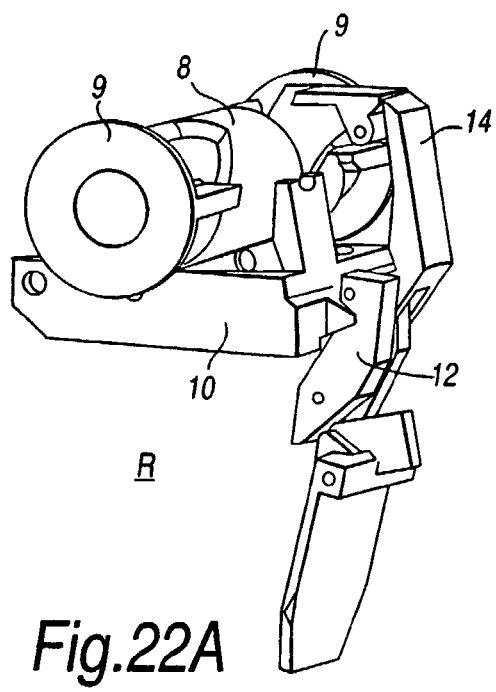
Figure 22B:
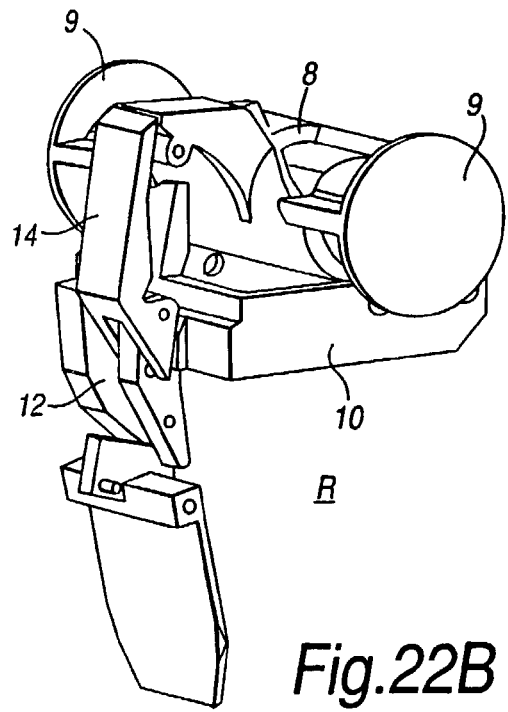

The sequence commences in state A as shown in FIG. 15 in which the torsion spring 7 has been loaded by depression of the buttons 9 and the spindle 8 is locked by the catch 14. In state A, the canister engagement lever is 10 held by the locking lever 12. The inhaler may be stored with the actuation mechanism 6 in state A.

At position B, the user starts to inhale. The flap 13, being responsive to such inhalation, starts to move. The shape of the contact surface 12b allows the locking lever 12 to start moving slowly. The actuation mechanism 6 is now in state C illustrated in FIG. 16.

At position D, the locking lever engagement surface 13a of the flap 13 releases the contact surface 12b of the locking lever 12. Accordingly, the canister engagement member 10 under the loading of the torsion spring 7 starts to rotate downwards deflecting the locking lever 12 against its reset spring as the projection 10f moves out of the notch 12a. The actuation mechanism is now in state E illustrated in FIG. 17.

At position F, the canister engagement lever 10 moves out of contact with the first contact surface 15a at the intermediate member 15 which therefore starts to move under the biassing of spring 16. However, the intermediate member 15 only moves a short way because at position G it is caught by the flap 13, in particular by the bar 13d of the flap 13 contacting the second contact surface 15b. This contact stops the movement of the flap 13 and the intermediate member 15.

The movement of the canister engagement lever 10 compresses the body 3 of the canister 2 relative to the stem 4 held in the nozzle block 11, thereby causing the canister 2 to deliver a dose of medicament. The nozzle block 11 directs the dose of medicament out of the mouthpiece at which the user is inhaling. The actuation mechanism 6 is now in state H illustrated in FIG. 18.

When the level of inhalation starts to fall, at position I the flap 13 under the biassing of its reset spring starts to move back closing the duct. This movement of the flap 13 causes the intermediate member 15 to move slightly due to the shape of the second contact surface 15*b*.

When the level of inhalation falls below the predetermined threshold, at position J the bar 13*d* of the flap 13 moves out of contact with the second contact surface 15*b*. This releases the intermediate member 15. Under the action of the spring 16, the intermediate member 15 moves to unload the spring 16. The actuation mechanism 6 is now in state K illustrated in FIG. 19.

At position L the load on the catch 14 from the spring 16 reduces to the extent that the catch 15 can no longer hold the spindle 8. The force of the torsion spring 7 forces the arm 8*c* of the spindle 8 upwards and out of engagement with the notch 14*a* of the catch 14. This forces the catch 14 backwards. The actuation mechanism 6 is now in state M illustrated in FIG. 20.

At position N, the torsion spring 7 reaches its neutral, unloaded position, so there is no load between the canister engagement lever 10 and the spindle 8. Thereafter the canister engagement lever 10 and the torsion spring 8 are moved under the action of the reset spring biassing the canister engagement lever 10.

At position O, the canister engagement lever 10 contacts the first contact surface 15*a* of the intermediate member 15 and forces it backwards. The actuation mechanism is now in state P illustrated in FIG. 21. This loads the spring 16 and pushes the catch 14 towards its locking position until the catch 14 contacts the arm 8*c* of the spindle 8 which has now passed out of the notch 14*a*.

At position Q, the projection 10*f* of the canister engagement lever 10 moves into the notch 12*a* of the locking lever 12 which snaps back into its locking position under the action of its reset spring. The actuation mechanism 6 is now in state R in FIG. 22. In state R, the canister is reset and ready to be compressed again for delivery of the next dose, but the actuation mechanism 6 is relaxed with the torsion spring 7 unloaded. The rotation of the spindle 8 has forced the buttons 9 outwards to the position illustrated in FIG. 22. The actuation mechanism 6 is ready to be loaded once again by compression of the buttons 9. The user is instructed to do this immediately after inhalation, so that the canister may be stored in a state ready to be used simply by inhaling at the mouthpiece 5.

When the user depresses the buttons 9 at position S, this drives the spindle 8 downwards. The arm 8*c* of the spindle 8 deflects the catch 14 slightly against the loaded spring 16 until the arm 8*c* moves into the notch 14*a*. This allows the spring 16 to snap the catch 14 into its locking position.

The invention claimed is:

1. A breath-actuated inhaler for delivery of a medicament by inhalation, the inhaler comprising:
    a canister which is compressible to deliver a dose of medicament;
    a housing for holding the canister and including a mouthpiece for delivery of a dose of medicament from the canister held in the housing, the canister having a valve stem; and
    an actuation mechanism for compressing the canister held in the housing in response to inhalation at the mouthpiece,
    wherein the housing includes two separable portions, the first portion housing the canister and the actuation mechanism and the second portion housing the mouthpiece and a duct shaped to direct an inhalation flow from the mouthpiece to the first portion for triggering the actuation mechanism, the duct enclosing a major portion of the air flow channel and defining an enclosed passage extending upstream of the valve stem towards an air inlet, and the second portion being separable from the first portion for allowing the mouthpiece and/or the duct to be replaced and/or removed for cleaning and the second portion and the duct being separately formed.

2. An inhaler according to claim 1, wherein the duct is separable from the second portion of the housing.

3. An inhaler according to claim 1, wherein the duct houses a nozzle block arranged to direct a dose of medicament delivered from a canister held in the inhaler out of the mouthpiece.

4. An inhaler according to claim 3, wherein the nozzle block and duct are separately formed.

5. An inhaler according to claim 3 wherein the nozzle block is configured to receive the valve stem and the duct is separable from the second portion of the housing and extends upstream of the nozzle block towards the air inlet.

6. An inhaler according to claim 1, wherein separation of the first and second portions of the housing allows replacement of the canister.

7. An inhaler according to claim 1, wherein the duct holds a nozzle block for holding the valve stem of the canister and directing medicament delivered from the canister out of the mouthpiece.

8. An inhaler according to claim 1, wherein the first portion of the housing has a flow inlet for receiving said inhalation flow and the duct is shaped to direct the inhalation flow to the flow inlet.

9. An inhaler according to claim 8, wherein the actuation mechanism includes a vane responsive to said inhalation flow for triggering the actuation mechanism and the first portion of the housing houses a further duct shaped to direct inhalation flow from the flow inlet to the vane.

10. A breath-actuated inhaler for delivery of a medicament by inhalation from a canister which is compressible to deliver a dose of medicament, the inhaler comprising:
    a housing for holding a canister, the housing including a mouthpiece for delivery of a dose of medicament from any canister held in the housing; and
    an actuation mechanism for compressing any canister held in the housing in response to inhalation at the mouthpiece,
    wherein the housing includes two separable portions, the first portion for housing a canister and the actuation mechanism and the second portion housing the mouthpiece and a duct shaped to direct an inhalation flow from the mouthpiece to the first portion for triggering the actuation mechanism, the duct enclosing a major portion of the air flow channel and defining an enclosed passage extending upstream of the valve stem towards an air inlet, and the second portion being separable from the first portion for allowing the mouthpiece or the duct to be replaced or removed for cleaning, the second portion and the duct being separately formed.

11. A breath-actuated inhaler for delivery of a medicament by inhalation from a canister which is compressible to deliver a dose of medicament, the inhaler comprising:
    a housing for holding a canister, the housing including a mouthpiece for delivery of a dose of medicament from any canister held in the housing; and
    an actuation mechanism for compressing any canister held in the housing in response to inhalation at the mouthpiece, wherein the housing includes two separable portions, the first portion for housing a canister and the actuation mechanism and the second portion housing the mouthpiece and a duct shaped to direct an inhalation flow from the mouthpiece to the first portion for triggering the actuation mechanism, the duct enclosing a major portion of the air flow channel and defining an enclosed passage extending upstream of the valve stem towards an air inlet, the duct being separable from the second portion of the housing, and the second portion being separable from the first portion for allowing the mouthpiece and/or the duct to be replaced and/or removed for cleaning.

* * * * *